(12) United States Patent
Youker et al.

(10) Patent No.: US 8,369,945 B2
(45) Date of Patent: Feb. 5, 2013

(54) IMPLANTABLE CARDIOVERTER DEFIBRILLATOR WITH PROGRAMMABLE CAPACITOR CHARGING LEVEL

(75) Inventors: Nick A. Youker, River Falls, WI (US); Kenneth N. Hayes, Blaine, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/190,107

(22) Filed: Jul. 25, 2011

(65) Prior Publication Data

US 2011/0282407 A1   Nov. 17, 2011

Related U.S. Application Data

(63) Continuation of application No. 11/126,951, filed on May 11, 2005, now Pat. No. 8,005,541.

(51) Int. Cl.
*A61N 1/39* (2006.01)

(52) U.S. Cl. .............. 607/5; 607/4; 607/29; 607/30; 607/7

(58) Field of Classification Search .......... 607/5, 7, 607/4, 29, 30
See application file for complete search history.

(56) References Cited

U.S. PATENT DOCUMENTS

| | | | |
|---|---|---|---|
| 5,115,807 A | 5/1992 | Pless et al. | |
| 5,215,081 A | 6/1993 | Ostroff | |
| 5,395,373 A | 3/1995 | Ayers | |
| 5,591,211 A * | 1/1997 | Meltzer | 607/5 |
| 5,741,307 A | 4/1998 | Kroll | |
| 5,836,971 A | 11/1998 | Starkweather | |
| 5,851,220 A | 12/1998 | Murphy | |
| 5,954,753 A | 9/1999 | Alt et al. | |
| 5,978,707 A | 11/1999 | Krig et al. | |
| 6,088,616 A | 7/2000 | Olson et al. | |
| 6,108,579 A | 8/2000 | Snell et al. | |
| 6,151,524 A | 11/2000 | Krig et al. | |
| 6,246,906 B1 | 6/2001 | Hsu et al. | |
| 6,317,632 B1 | 11/2001 | Krig et al. | |
| 6,426,628 B1 | 7/2002 | Palm et al. | |
| 6,430,449 B1 | 8/2002 | Hsu et al. | |
| 6,556,862 B2 | 4/2003 | Hsu et al. | |
| 6,587,720 B2 | 7/2003 | Hsu et al. | |
| 6,751,502 B2 | 6/2004 | Daum et al. | |

(Continued)

FOREIGN PATENT DOCUMENTS

| | | |
|---|---|---|
| JP | 6323675 | 1/1988 |
| WO | WO-2006002147 A2 | 1/2006 |

(Continued)

OTHER PUBLICATIONS

"U.S. Appl. No. 11/126,951, Advisory Action mailed Apr. 26, 2010", 5 pgs.

(Continued)

*Primary Examiner* — Joseph Stoklosa
(74) *Attorney, Agent, or Firm* — Schwegman Lundberg & Woessner, P.A.

(57) ABSTRACT

An implantable cardioverter defibrillator (ICD) has a programmable ICD energy level corresponding to the maximum defibrillation energy deliverable with each defibrillation shock pulse. The ICD energy level is programmable within the maximum energy capacity of the defibrillation capacitor (s) of the ICD. In various embodiments, after a user enters the ICD energy level, one or more corresponding ICD performance parameters are presented. Restrictions are applied to the energy level programming of the ICD to ensure the predictability of the one or more ICD performance parameters.

20 Claims, 8 Drawing Sheets

U.S. PATENT DOCUMENTS

| | | |
|---|---|---|
| 6,873,873 B2 | 3/2005 | Hsu et al. |
| 7,113,824 B2 | 9/2006 | Krig et al. |
| 8,005,541 B2 | 8/2011 | Youker et al. |
| 2002/0143372 A1 | 10/2002 | Snell et al. |
| 2003/0199927 A1 | 10/2003 | Ousdigian et al. |
| 2003/0199929 A1 | 10/2003 | Snyder et al. |
| 2005/0149135 A1 | 7/2005 | Krig et al. |
| 2005/0192640 A1 | 9/2005 | Ousdigian et al. |
| 2006/0259082 A1 | 11/2006 | Youker et al. |

FOREIGN PATENT DOCUMENTS

| | | |
|---|---|---|
| WO | WO-2006122198 A2 | 11/2006 |
| WO | WO-2006122198 A3 | 11/2006 |

OTHER PUBLICATIONS

"U.S. Appl. No. 11/126,951, Advisory Action mailed Dec. 19, 2008", 4 pgs.

"U.S. Appl. No. 11/126,951, Final Office Action mailed Sep. 18, 2008", 8 pgs.

"U.S. Appl. No. 11/126,951, Final Office Action mailed Dec. 28, 2009", 8 pgs.

"U.S. Appl. No. 11/126,951, Non-Final Office Action mailed Feb. 27, 2008.", 8 pgs.

"U.S. Appl. No. 11/126,951, Notice of Allowance mailed Apr. 1, 2011", 7 pgs.

"U.S. Appl. No. 11/126,951, Respone filed Aug. 12, 2009 to Non-Final Office Action mailed May 12, 2009", 16 pgs.

"U.S. Appl. No. 11/126,951, Response filed May 27, 2008 to Non Final Office Action mailed Feb. 27, 2008", 18 pgs.

"U.S. Appl. No. 11/126,951, Response filed Dec. 9, 2008 to Final Office Action mailed Sep. 18, 2008", 17 pgs.

"U.S. Appl. No. 11/126,951, Response filed Feb. 18, 2009 to Final Office Action mailed Sep. 18, 2008", 18 pgs.

"U.S. Appl. No. 11/126,951, Response filed Mar. 22, 2010 to Final Office Action mailed Dec. 28, 2009", 16 pgs.

"U.S. Appl. No. 11/126,951, Response filed May 24, 2010 to Final Office Action mailed Dec. 28, 2009", 17 pgs.

"U.S. Appl. No. 11/126,951, Response filed Aug. 12, 2009 to Non Final Office Action May 12, 2009", 16 pgs.

"U.S. Appl. No. 11/126,951, Non-Final Office Action mailed May 12, 2009", 9 pgs.

"European Application Serial No. 06759505.8, Office Action mailed Mar. 31, 2008", 7 pgs.

"European Application No. 06759505.8, Office Action mailed May 13, 2009", 6 pgs.

"Invitation to Pay Additional Fees for U.S. Application No. PCT/US2006/018115, Date mailed Oct. 13, 2006", 8 Pages.

"U.S. Appl. No. 11/126,951, 312 Amendment filed Jun. 30, 2011", 11 pgs.

"U.S. Appl. No. 11/126,951, PTO Response to 312 Amendment mailed Jul. 21, 2011", 2 pgs.

"U.S. Appl. No. 13/190,107, Restriction Requirements mailed Feb. 17, 2012", 7 pgs.

"European Application Serial No. 06759505.8, Response filed Feb. 20, 2012 to Summons to Attend Oral Proceedings mailed Nov. 18, 2011", 10 pgs.

"European Application Serial No. 06759505.8, Summons to Attend Oral Proceeding dated Nov. 18, 2011", 6.

"Japanese Application Serial No. 2008-511327, Office Action mailed Nov. 15, 2011", 7 pgs.

"Japanese Application Serial No. 2008-511327, Response filed Apr. 13, 2012 to Office Action mailed Nov. 17, 2011", English Claims with response, 17 pgs.

\* cited by examiner

IMPLANTABLE CARDIOVERTER DEFIBRILLATOR WITH PROGRAMMABLE CAPACITOR CHARGING LEVEL

CLAIM OF PRIORITY

This application is a continuation of and claims the benefit of priority tinder 35 U.S.C, §120 to U.S. patent Application Ser. No. 11/126,951, filed on filed May 11, 2005, now issued as U.S. Pat. No. 8,005,541, which is hereby incorporated by reference herein in its entirety.

TECHNICAL FIELD

This document generally relates to cardiac rhythm management (CRM) systems and particularly to an implantable cardioverter defibrillator (ICD) having a maximum defibrillation energy level that is programmable.

BACKGROUND

Tachyarrhythmias are abnormal heart rhythms characterized by a rapid heart rate. Tachyarrhythmias generally include supraventricular tachycardia (SVT, including atrial tachycardia, AT) and ventricular tachycardia (VT). Fibrillation is a form of tachycardia further characterized by an irregular heart rhythm. In a normal heart, the sinoatrial node, the heart's predominant natural pacemaker, generates electrical impulses that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. VT occurs when the electrical impulses re-enter the atria from the ventricles to form a self-sustaining conductive loop or when a natural pacemaker in a ventricle usurps control of the heart rate from the sinoatrial node. When the heart rate reaches certain levels, the ventricles contract before they are properly filed with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Implantable cardioverter defibrillators (ICDs) are used to treat most tachyarrhythmias, including AT, VT, and VF. An ICD is an implantable medical device that delivers an electric shock pulse to terminate a detected tachyarrhythmia episode. The electric shock pulse depolarizes portions of the myocardium and renders it refractory. The energy of the shock pulse is provided by one or more defibrillation capacitors of the ICD. Following a detection of an episode of tachyarrhythmia, the one or more defibrillation capacitors are charged to a programmed capacitor charging level in preparation of the possible delivery of a shock pulse. The maximum defibrillation energy level of the LCD, referred to as the ICD energy level, is the maximum level up to which the capacitor charging level can be programmed. Thus, the ICD energy level determines the maximum amount of energy deliverable with each shock pulse.

During the implantation of an ICD to a patient anticipating tachyarrhythmia episodes, a defibrillation threshold (DFT) test is performed to determine the DFT, which is the energy level of the shock pulse required to terminate a tachyarrhythmia episode of that patient. The energy level of each shock pulse is then programmed to a level exceeding the DFT by a safety margin. The programmable energy level for each shock pulse is limited to the ICD energy level. Thus, an ICD with an ICD energy level higher than the patient's DFT by the safety margin is to be chosen for the patient.

For an ICD, a higher energy level means bigger size, longer capacitor charging time (and hence longer delay in responding to a tachyarrhythmia detection), and shorter device longevity. Because the DFT varies significantly from patient to patient, there is a need for ICDs that are energy-efficient over a range of substantially different DFTs.

SUMMARY

An ICD has a programmable ICD energy level corresponding to the maximum defibrillation energy deliverable with each defibrillation shock pulse. The ICD energy level is programmable within the maximum energy capacity of the defibrillation capacitor(s) of the ICD.

In one embodiment, a CRM system includes an ICD and an external system for communicating with the ICD. The ICD includes a defibrillation circuit and an energy level control module. The defibrillation circuit delivers defibrillation shock pulses. The energy level control module controls an ICD energy level based on one or more programming parameters. The ICD energy level is related to a maximum defibrillation energy of each of the defibrillation shock pulses. The external system includes an ICD energy level programming module, an ICD performance estimation module, and a user interface. The ICD energy level programming module produces the one or more programming parameters based on an energy level selection. The ICD performance estimation module produces one or more estimated ICD performance parameters based on the energy level selection. The user interface includes a user input device to receive the energy level selection and a presentation device to visually present the one or more estimated ICD performance parameters.

In one embodiment, an ICD includes a defibrillation circuit and an implant controller. The defibrillation circuit delivers defibrillation shock pulses and includes a defibrillation capacitor and a capacitor charging circuit. The defibrillation capacitor stores an energy for each of the defibrillation shock pulses. The capacitor charging circuit charges the defibrillation capacitor in preparation for the delivery of each of the defibrillation shock pulses. The implant controller includes a parameter receiver and an energy level control module. The parameter receiver receives one or more programming parameters. The energy level control module controls an ICD energy level based on the one or more programming parameters. The ICD energy level controls a maximum charging level of the defibrillation capacitor.

In one embodiment, an external system for communicating with an ICD includes an ICD energy level programming module, an ICD performance estimation module, and a user interface. The ICD energy level programming module programs an ICD energy level. The ICD energy level is related to a maximum defibrillation energy level deliverable by the ICD based on an energy level selection. The ICD performance estimation module produces one or more estimated ICD performance parameters based on the energy level selection. The user interface includes a user input device to receive the energy level selection and a presentation device to visually present the one or more estimated ICD performance parameters.

In one embodiment, a method for operating an ICD is provided. One or more programming parameters are received from an external system communicating with the ICD. An ICD energy level is controlled based on the one or more programming parameters. The ICD energy level is a maximum defibrillation energy level deliverable by the ICD.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
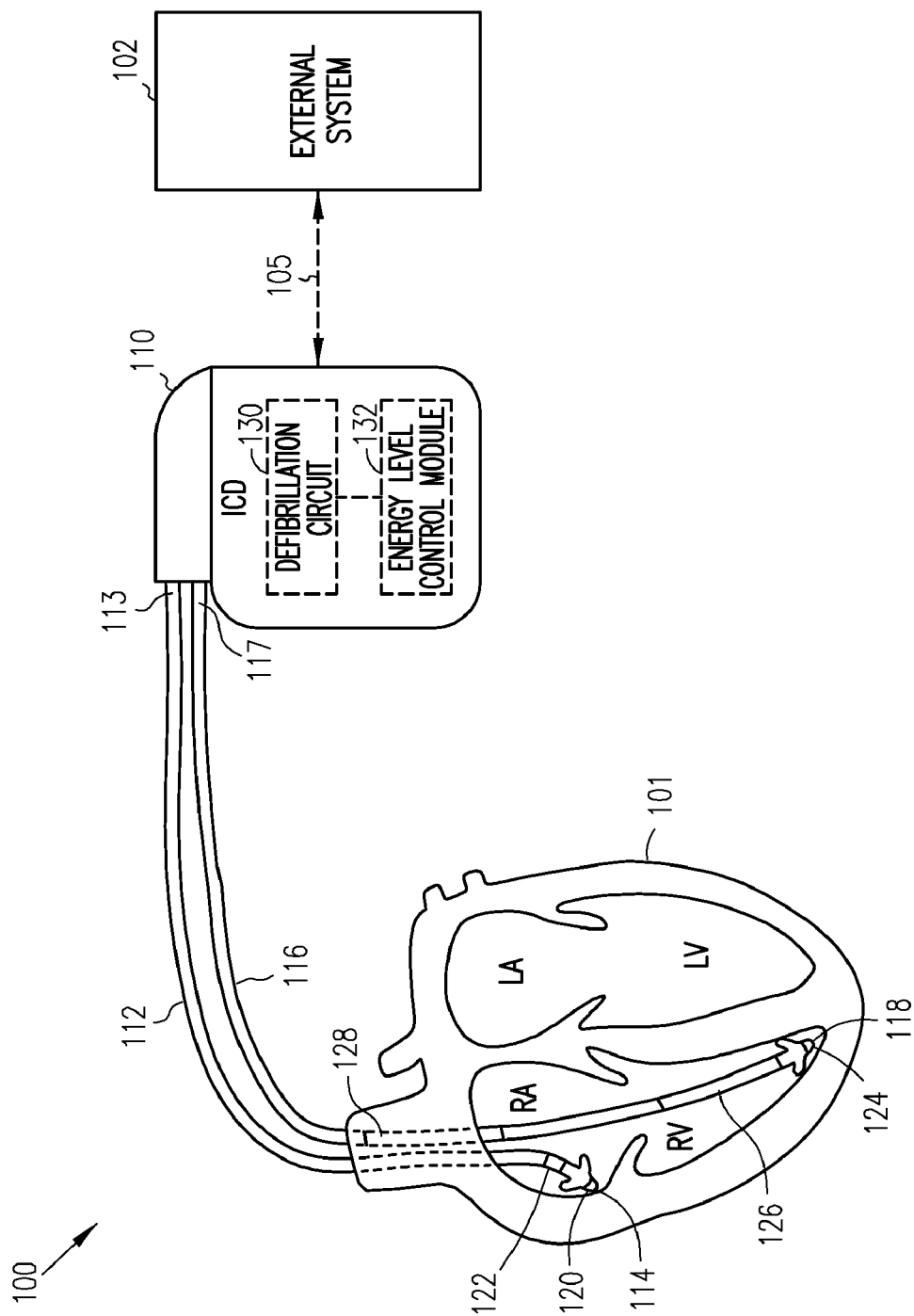
FIG. 1 is an illustration of a CRM system and portions of an environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

A factor that substantially affects an ICD's energy efficiency is the difference between the ICD energy level and the shock pulse energy level. The ICD energy level represents the maximum amount of energy deliverable with each defibrillation shock pulse. The shock pulse energy level is the amount of energy programmed for delivery with each defibrillation shock pulse. The ICD's energy efficiency is increased by decreasing the difference between the ICD energy level and the shock pulse energy level.

One method to maximize the energy efficiency for ICDs is to make two or more device versions available for each type of ICD. These device versions have fixed ICD energy levels that are substantially distinctive in value. After a patient's DFT is measured and the shock pulse energy level is determined, the most energy-efficient ICD for this patient is the device version with the lowest ICD energy level. The lowest energy level is an ICD energy level that is equal to or higher than the shock pulse energy level to be programmed. For example, a physician prescribes a certain type of ICD for the patient. That type of ICD is available as a high-energy ICD (with a higher ICD energy level) and a low-energy ICD (with a lower ICD energy level). Based on the available information for the patient and medical judgment, the physician chooses the low-energy ICD to start with. During the operation for the implantation of the ICD, the low-energy ICD is used to perform the DFT test. Based on the measured DFT, the physician determines a shock pulse energy level for the patient. If the low-energy ICD is capable of providing for this shock pulse energy level, it is implanted for long-term use in the patient. If the physician is unable to complete the DFT with the low-energy ICD because the ICD energy level is too low, or if the low-energy ICD is incapable of providing for the shock pulse energy level with a desirable safety margin, the physician replaces the low-energy ICD with the high-energy ICD. For a patient treatable with the low-energy ICD, using the low-energy ICD benefits the patient by providing a shorter capacitor charging time and a longer device longevity. However, if the physician concluded that the high-energy ICD must be used after the DFT test, the low-energy device first used for the DFT test is wasted and cannot be used in a different patient. This increases the overall cost of ICD therapies. The waste can be more significant when ICDs with more than two energy levels are made available.

According to the present subject matter, an ICD has a programmable ICD energy level. The ICD includes one or more defibrillation capacitors that provide for a maximum ICD energy level. With certain restrictions, the physician is allowed to program the ICD for a desirable ICD energy level up to the maximum ICD energy level. The shock pulse energy level is then programmable within the programmed ICD energy level. The capacitor charging time and the longevity of the ICD are then determined by the programmed ICD energy level. The size of the ICD is determined by the maximum ICD energy level. However, with advanced capacitor technology, benefits associated with the shortened capacitor charging time and increased device longevity substantially outweigh the disadvantages associated with the increased size. In one embodiment, the ICD with the energy level programmability is pre-programmed for a relatively low or moderate energy level by the manufacturer. The low or moderate energy level is empirically determined to satisfy the need of defibrillation for the majority of a patient population. If a patient has a particularly high DFT, or a high safety margin for defibrillation energy is desired, the physician programs the ICD for a higher ICD energy level. In one embodiment, the energy level programmability is implemented using software in the ICD and its programmer, and does not affect the ICD's energy efficiency after the ICD energy level is programmed.

In a specific example, without the energy level programmability, versions of a particular type ICD include a high-energy ICD that has a 41-joule energy level ("41-J ICD") and a low-energy ICD that has a 31-joule energy level ("31-J ICD"). The 41-J ICD has a size of 32 cubic centimeters (cc), a predicted longevity of 5.5 years, and a beginning-of-life (BOL) capacitor charging time of 8.5 seconds. The BOL capacitor charging time refers to the time required to fully charge the defibrillation capacitor(s) of the ICD when the battery is new (in the "BOL" stage). The 31-J ICD has a size of 29 cc, a predicted longevity of 6.5 years, and a beginning-of-life (BOL) capacitor charging time of 6.5 seconds. According to the present subject matter, an ICD with the energy level programmability eliminates the need for the two versions. The ICD with the energy level programmability is produced based on the 41-J ICD by providing programmability to one or more device parameters such as the maximum energy level and the reform energy level. The physician is to choose between 41 joules and 31 joules as the ICD energy level. If the physician programs the ICD energy level to 41 joules, the ICD operates as the 41-J ICD in terms of the energy efficiency, predicted longevity, and capacitor charging time. If the physician programs the ICD energy level to 31 joules, the ICD operates as the 31-J ICD in terms of the energy efficiency, predicted longevity, and capacitor charging time. When leaving factory, the ICD with the energy level programmability is pre-programmed for operating as a 31-J ICD. If a patient has a particularly high DFT as determined during the DFT testing, or a high safety margin is desired, the physician programs the ICD for operating as a 41-J ICD. The parameters given in this specific example are realistic numbers based on ICDs of Cardiac Pacemakers, Inc. (4100 Hamline Avenue North, Saint Paul, Minn. 55112).

To ensure certainty with respect to the ICD's predicted device longevity, one or more restrictions are applied to the physician's ability to program the ICD energy level. Such restrictions are given in terms of time, number of reprogramming, and/or number of shock pulses delivered. Exceptions are permitted under strict conditions, such as by the manufacturer of the device upon reviewing specific circumstances.

The ICD with the energy level programmability provides the physician with the flexibility of adjusting the device performance based on the needs and conditions of each individual patient without the need to switch between ICDs with different energy levels. This significantly reduces the cost associated with designing, manufacturing, and managing inventories of multiple device models, while having the potential for increased customer satisfaction by providing simplified implantation procedure and/or enhanced device performance controlled by physicians.

FIG. 1 is an illustration of one embodiment of a CRM system 100 and portions of the environment in which CRM system 100 operates. CRM system 100 includes an ICD 110 that is electrically coupled to a heart 101 through leads 112 and 116. An external system 102 communicates with ICD 110 via a telemetry link 105.

ICD 110 is an implantable medical device that includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 101 and delivers pacing and cardioversion/defibrillation shock pulses to heart 101. Lead 112 is a pacing lead that includes a proximal end 113 connected to ICD 110 and a distal end 114 disposed in the right atrium (RA) of heart 101. A pacing-sensing electrode 120 is located at distal end 114. Another pacing-sensing electrode 122 is located near distal end 114. Electrodes 120 and 122 are electronically connected to ICD 110 to allow sensing of the atrial electrogram and/or delivery of atrial pacing pulses. Lead 116 is a pacing/defibrillation lead that includes a proximal end 117 connected to ICD 110 and a distal end 118 disposed in the right ventricle (RV) of heart 101. A pacing-sensing electrode 124 is located at distal end 118. A defibrillation electrode 126 is located near distal end 118 but electrically separated from pacing-sensing electrode 124. Another defibrillation electrode 128 is located at a distance from distal end 118 for supraventricular placement. Electrodes 124, 126, and 128 are electrically connected to ICD 110. Electrode 124 allows sensing of the ventricular electrogram and/or delivery of ventricular pacing pulses. Electrodes 126 and 128 allow delivery of cardioversion/defibrillation shock pulses to heart 101.

ICD 110 is an ICD with energy level programmability and includes a defibrillation circuit 130 and an energy level control module 132. Defibrillation circuit 130 delivers shock pulses to heart 101. Energy level control module 132 provides ICD 110 with the energy level programmability by controlling the ICD energy level. The ICD energy level limits the maximum amount of energy deliverable by defibrillation circuit 130 with each shock pulse. According to the present subject matter, the ICD energy level is programmable, using external system 102, to a level limited by the maximum energy capacity of defibrillation circuit 130. After the ICD energy level is programmed, the amount of energy delivered with each shock pulse is programmable to a shock pulse energy level up to the ICD energy level.

External system 102 allows for programming of ICD 110 and receives signals acquired by ICD 110. In one embodiment, external system 102 includes a programmer. In another embodiment, external system 102 is a patient management system such as the system illustrated in FIG. 7. In one embodiment, telemetry link 105 is an inductive telemetry link. In an alternative embodiment, telemetry link 105 is a far-field radio-frequency telemetry link. Telemetry link 105 provides for data transmission from ICD 110 to external system 102. This may include, for example, transmitting real-time physiological data acquired by ICD 110, extracting physiological data acquired by and stored in ICD 110, extracting therapy history data stored in ICD 110, and extracting data indicating an operational status of ICD 100 (e.g., battery status and lead impedance). Telemetry link 105 also provides for data transmission from external system 102 to ICD 110. This may include, for example, programming ICD 110 to acquire physiological data, programming ICD 110 to perform at least one self-diagnostic test (such as for a device operational status), programming ICD 110 to run a signal analysis algorithm (such as an algorithm implementing the tachycardia detection and classification methods discussed in this document), programming ICD 110 to deliver pacing and/or cardioversion/defibrillation therapies, and programming ICD 110 to changes the ICD energy level.

Figure 2:
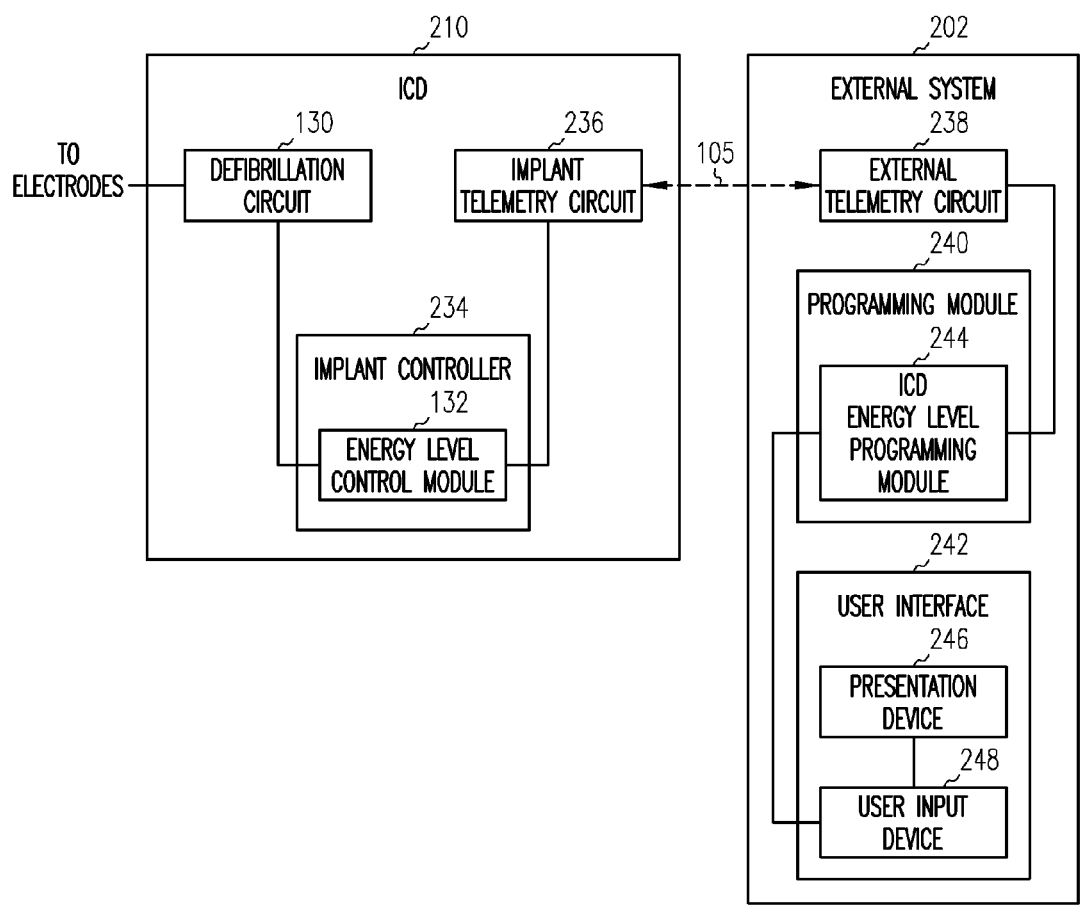
FIG. 2 is a block diagram illustrating an embodiment of portions of a circuit of the CRM system.

FIG. 2 is a block diagram illustrating an embodiment of portions of a circuit of CRM system 100, including an ICD 210 and an external system 202. ICD 210 is an ICD with the energy level programmability and a specific embodiment of ICD 110. External system 202 allows programming of the ICD energy level of ICD 210 and is a specific embodiment of external system 102.

ICD 210 includes defibrillation circuit 130, an implant controller 234, and implant telemetry circuit 236. Defibrillation circuit 130 delivers shock pulses to heart 101 through electrodes such as those illustrated in FIG. 1. Implant controller 234 controls the operation of ICD 210 and includes energy level control module 132. Implant telemetry circuit 236 receives data from external system 202, including one or more programming parameters related to the ICD energy level of LCD 210. Energy level control module 132 controls the ICD energy level of ICD 210 based on the received one or more programming parameters. The ICD energy level determines the maximum amount of defibrillation energy delivered by defibrillation circuit 130 with each of the shock pulses. The ICD energy level is programmable up to the maximum energy capacity of defibrillation circuit 130. After the ICD energy level is programmed to a certain level, the amount of defibrillation energy for each shock pulse is programmable to an amount up to that certain level.

External system 202 includes an external telemetry circuit 238, a programming module 240, and a user interface 242. External telemetry circuit 238 and implant telemetry circuit 236 support telemetry link 105, through which external system 202 and ICD 210 communicates. Programming module 240 allows programming of ICD 210 and includes an ICD energy level programming module 244. ICD energy level programming module 244 produces the one or more programming parameters related to the ICD energy level of LCD 210 based on an energy level parameter entered by a user. User interface 242 includes a presentation device 246 and a user input device 248. User input device 248 receives the energy level parameter. In one embodiment, user input device 248 allows the user to enter an energy level parameter within a predetermined range of energy levels. In another embodiment, user input device allows the user to selected an energy level parameter from a plurality of predetermined ICD energy levels.

Figure 3:
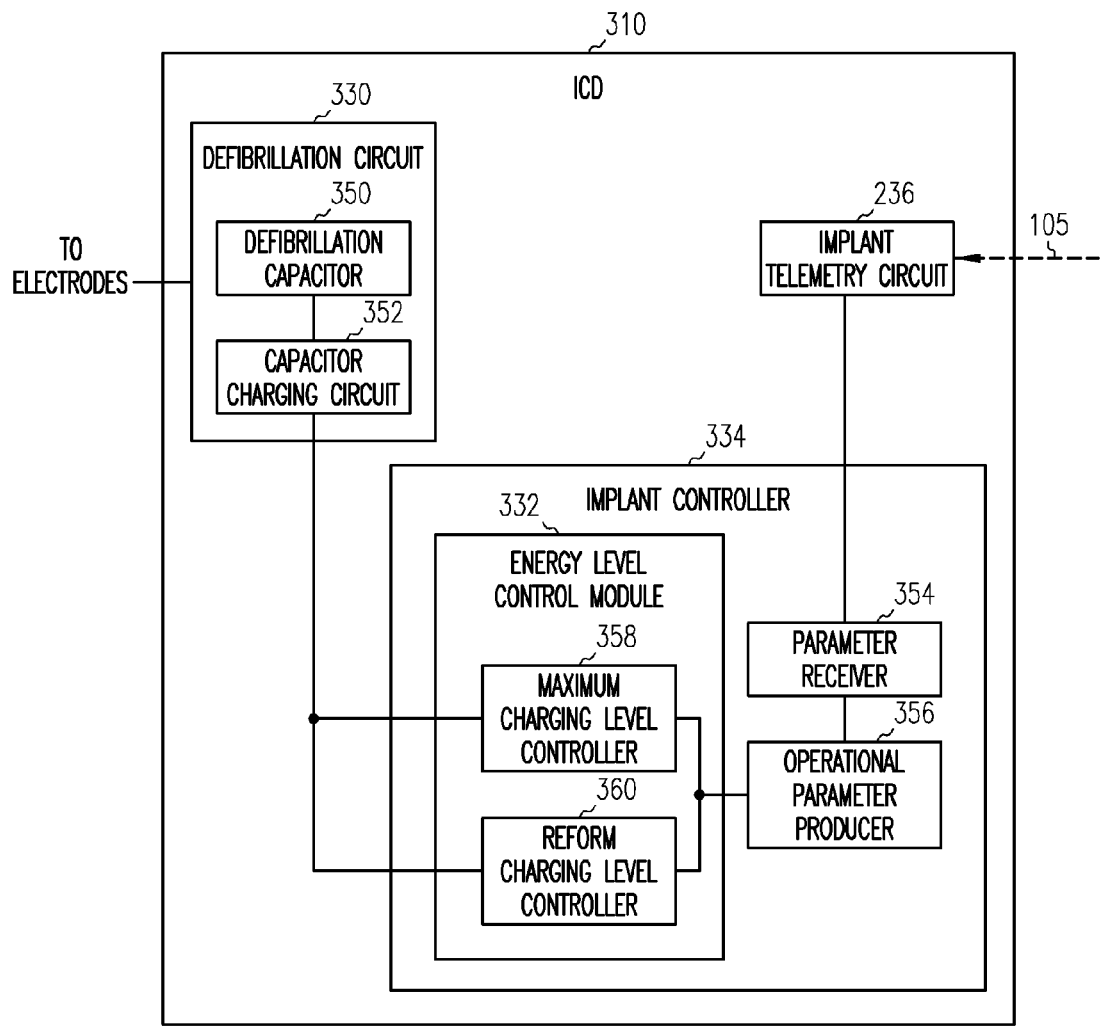
FIG. 3 is a block diagram illustrating an embodiment of portions of a circuit of an ICD of the CRM system.

FIG. 3 is a block diagram illustrating an embodiment of portions of a circuit of an ICD 310, which is an ICD with the energy level programmability and a specific embodiment of ICD 210. ICD 310 includes a defibrillation circuit 330, an implant controller 334, and implant telemetry circuit 236.

Defibrillation circuit 330 is a specific embodiment of defibrillation circuit 230 and includes a defibrillation capacitor 350 and a capacitor charging circuit 352. Defibrillation capacitor 350 represents one or more defibrillation capacitors of ICD 310 that store the energy for delivering to heart 101 with each of the shock pulses. The energy capacity of defibrillation capacitor 350 is the energy capacity of defibrillation circuit 330, which determines the limit to which the ICD energy level of ICD 330 can be programmed. Capacitor charging circuit 352 charges defibrillation capacitor 350 in preparation for the delivery of each of the shock pulses. In one embodiment, defibrillation capacitor 350 has an energy density of approximately 6.50 J/cc. This translates to about 1.5 cc per 10 joules. Thus, for patient who would otherwise need an ICD with a relatively low, fixed ICD energy level, the cost of additional size for using an ICD with the energy level programmability is reasonably small. In a specific embodiment, ICD 310 has an ICD energy level programmable between approximately 31 joules and 41 joules. Defibrillation capacitor 350 is capable of providing for 41 joules of defibrillation energy for each of the shock pulses and has a volume of approximately 6.3 cc. The volume of a defibrillation capacitor providing for 31 joules of energy is approximately 4.8 cc. For a patient who could otherwise use a 31-J ICD, the additional capacitor size is approximately 1.5 cc. Such an additional size translates to an additional ICD device size that is insignificant, especially when considering with the overall benefits provided by the energy level programmability.

Implant controller 334 includes an energy level control module 332, a parameter receiver 354, and an operational parameter producer 356. Energy level control module 332 is a specific embodiment of energy level control module 232 and includes a maximum charging level controller 358 and a reform charging level controller 360. Maximum charging level controller 358 controls the maximum charging level of defibrillation capacitor 350, which is the maximum energy level to which defibrillation capacitor 350 is charged by capacitor charging circuit 352 before the delivery of a shock pulse. Reform charging level controller 360 controls a reform charging level of defibrillation capacitor 350, which is the energy level to which defibrillation capacitor 350 is charged by capacitor charging circuit 352 in a forming process when no shock pulse is being delivered. The maximum charging level and the reform charging level are each associated with the ICD energy level. Parameter receiver 354 receives the one or more programming parameters related to the ICD energy level from implant telemetry circuit 236. In one embodiment, parameter receiver 354 receives an ICD energy level parameter specifying the ICD energy level that is transmitted to ICD 310 via telemetry link 105. Operational parameter producer 356 produces one or more ICD operational parameters including the maximum charging level and the reforming charging level based on the ICD energy level parameter received. In another embodiment, parameter receiver 354 receives one or more ICD operational parameters controlling the ICD energy level, including the maximum charging level and the reforming charging level, that are transmitted to ICD 310 via telemetry link 105.

Figure 4:
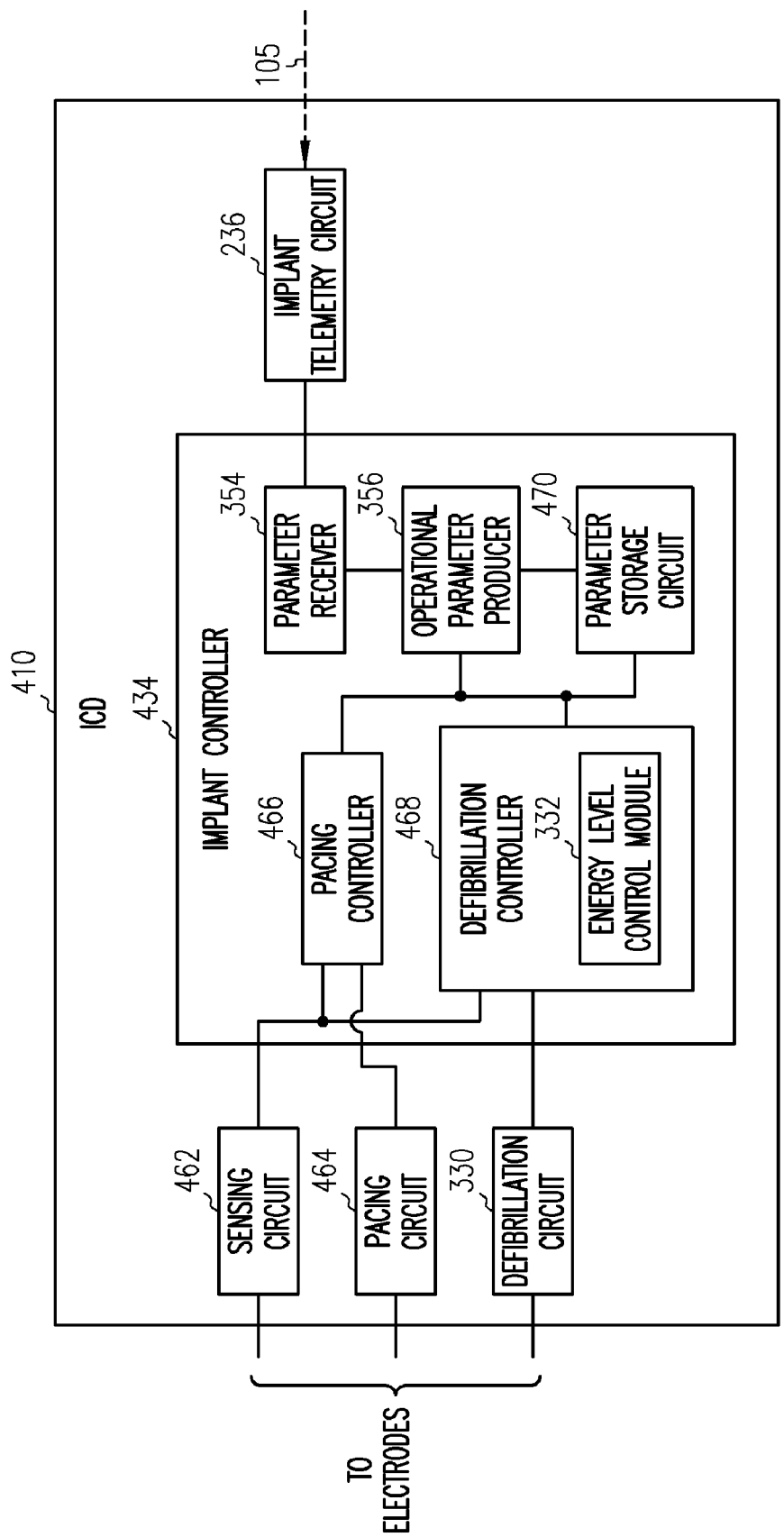
FIG. 4 is a block diagram illustrating a specific embodiment of portions of the circuit of the ICD.

FIG. 4 is a block diagram illustrating a specific embodiment of portions of the circuit of an ICD 410, which is an ICD with the energy level programmability and a specific embodiment of ICD 310. ICD 410 includes a sensing circuit 462, a pacing circuit 464, defibrillation circuit 330, an implant controller 434, and implant telemetry circuit 236.

Sensing circuit 462 senses one or more cardiac signals from heart 101. Pacing circuit 464 delivers pacing pulses to heart 101. Defibrillation circuit 330 delivers shock pulses to heart 101. The one or more cardiac signals are sensed, and the pacing and shock pulse are delivered, using electrodes such as those illustrated in FIG. 1. In various embodiments, the electrodes include endocardial and/or epicardial electrodes.

Implant controller 434 includes a pacing controller 466, a defibrillation controller 468, parameter receiver 354, operational parameter producer 356, and a parameter storage circuit 470. Pacing controller 466 controls the delivery of pacing pulses by executing a pacing algorithm. In one embodiment, pacing controller 466 includes a cardiac resynchronization therapy (CRT) controller to control the delivery of pacing pulses by executing a CRT pacing algorithm. In another embodiment, pacing controller 466 includes a cardiac remodeling control therapy (RCT) controller to control the delivery of pacing pulses by executing a RCT pacing algorithm. Defibrillation controller 468 controls the delivery of the shock pulses by detecting and classifying tachyarrhythmias based on at least one cardiac signal sensed by sensing circuit 462. Defibrillation controller 468 includes energy level control module 332, which controls the ICD energy level of ICD 410 based on the ICD operational parameters including the maximum charging level and the reforming charging level. In one embodiment, parameter storage circuit 470 stores sets of values for the ICD operational parameters. Each set of the values corresponding to an ICD energy level. After the ICD energy level is received by parameter receiver 354, operational parameter producer 356 selects a set of the values for the ICD operational parameters stored in parameter storage circuit 470 based on the received ICD energy level.

In one embodiment, implant controller 234, 334, or 434 includes a microprocessor or microcontroller circuit, and energy level control module 132 or 332 is implemented by software running on the microprocessor or microcontroller circuit. In another embodiment, energy level control module 132 or 332 is implemented by hardware such as portions of an application specific integrated circuit or a programmable logic circuit. In another embodiment, energy level control module 132 or 332 is implemented by a combination of hardware and software.

Figure 5:
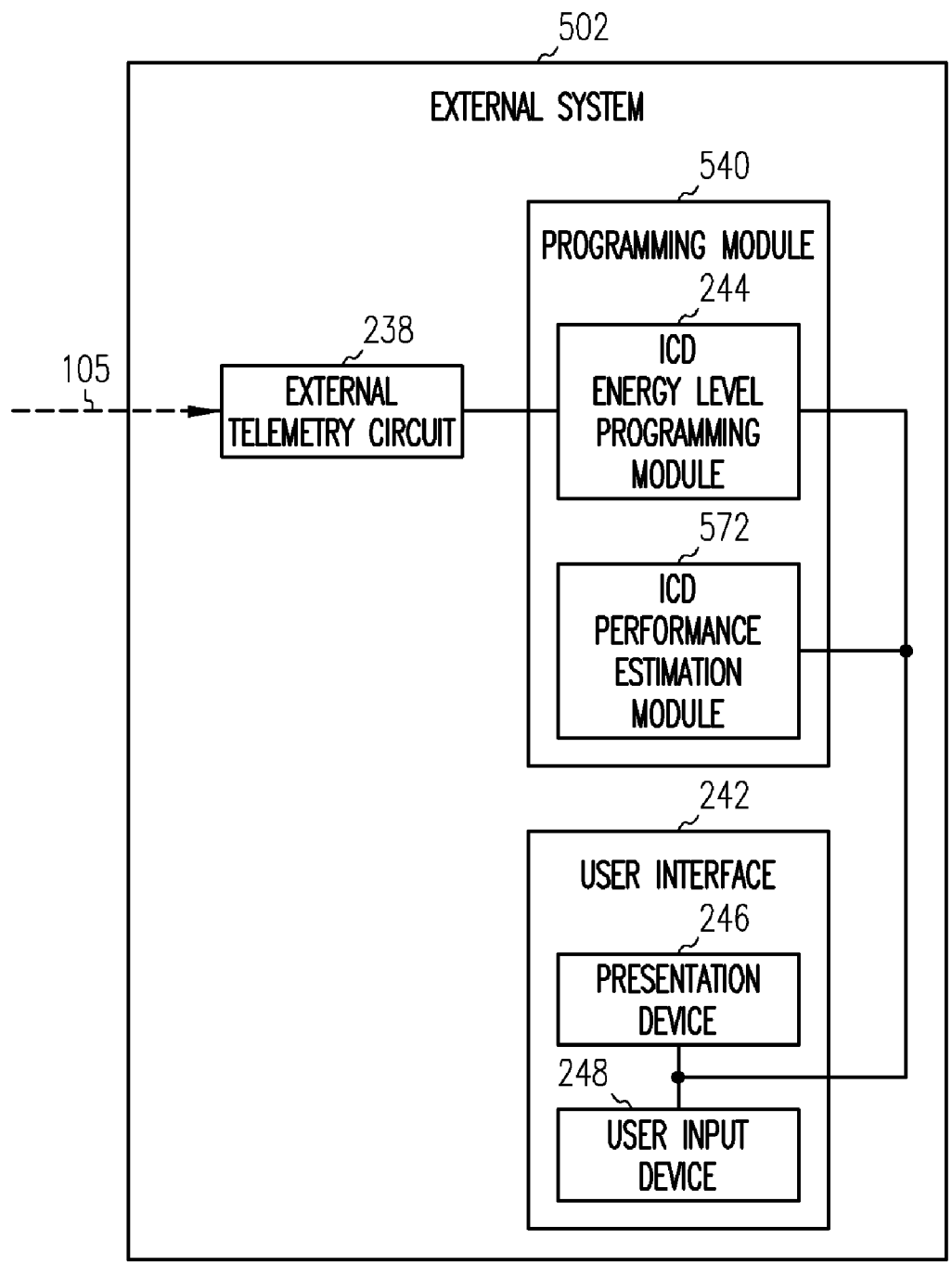
FIG. 5 is a block diagram illustrating an embodiment of portions of a circuit of an external system of the CRM system.

FIG. 5 is a block diagram illustrating an embodiment of portions of the circuit of an external system 502 for programming an ICD such as ICD 110 or any of its specific embodiments. External system 502 is a specific embodiment of external system 202 and includes external telemetry circuit 238, a programming module 540, and user interface 242.

Programming module 540 is a specific embodiment of programming module 240. In addition to ICD energy level programming module 244, programming module 540 includes an ICD performance estimation module 572. After the energy level parameter is received by user input device 248, ICD performance estimation module 572 produces one or more estimated ICD performance parameters based on the received energy level parameter. Presentation device 246 visually presents the one or more estimated ICD performance parameters. In one embodiment, ICD performance estimation module 572 produces estimated device longevity and capacitor charging time. The device longevity indicates the life expectancy of an ICD at the end of which the ICD is to be replaced if needed for the continued treatment of the patient. The capacitor charging time is the time required to charge the defibrillation capacitor(s) of the ICD before a shock pulse is delivered. The device longevity and the capacitor charging time are functions of the ICD energy level. By entering an energy level parameter through specifying a lower ICD energy level through user input device 248, the device longevity is increased, and the capacitor charging time is shortened.

Figure 6:
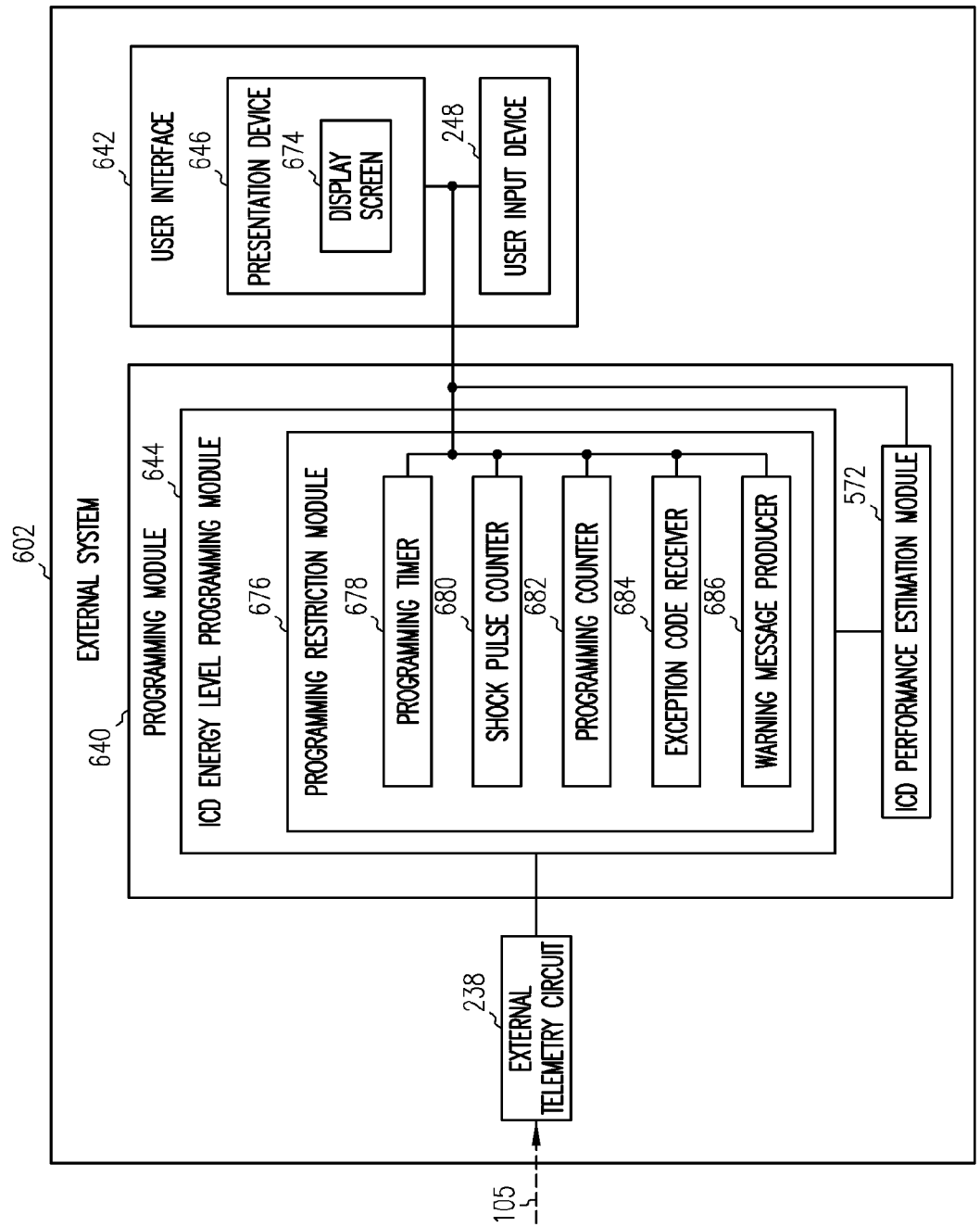
FIG. 6 is a block diagram illustrating a specific embodiment of portions of the circuit of the external system.

FIG. 6 is a block diagram illustrating a specific embodiment of portions of a circuit of an external system 602 for programming an ICD such as ICD 110 or any of its specific embodiments. External system 602 is a specific embodiment of external system 502 and includes external telemetry circuit 238, a programming module 640, and a user interface 642.

Programming module 640 includes an ICD energy level programming module 644 and ICD performance estimation module 572. ICD energy level programming module 644 is a specific embodiment of ICD energy level programming module 244. In addition to producing the one or more programming parameters related to the ICD energy level and programming the ICD using the one or more programming parameters, ICD energy level programming module 644 includes a programming restriction module 676. Programming restriction module 676 allows the programming of the ICD energy level according to one or more predetermined restriction rules.

In one embodiment, as illustrated in FIG. 6, programming restriction module 676 includes a programming timer 678, a shock pulse counter 680, a programming counter 682, an exception code receiver 684, and a warning message producer 686. During the implantation of the ICD, external system 602 causes an initial activation of the ICD. Programming timer 678 times a time interval starting with the initial activation of the ICD, and programming restriction module 676 disallows the programming of the ICD energy level after the time interval reaches a predetermined programming time limit. Shock pulse counter 680 counts a number of defibrillation shock pulses delivered from the ICD since the initial activation of the ICD, and programming restriction module 676 disallows the programming of the ICD energy level after the number reaches a predetermined threshold number. Programming counter 682 counts a number of the programming of the ICD energy level performed since the initial activation of the ICD, and programming restriction module 676 disallows the programming of the ICD energy level after the number reaches a predetermined threshold number. In one embodiment, programming restriction module 676 allows the programming of the ICD energy level according to a predetermined exception to the one or more predetermined restriction rules after such programming is disallowed. In this embodiment, exception code receiver 684 receives an exception code permitting the programming of the ICD energy level according to the predetermined exception to the one or more predetermined restriction rules. Warning message producer 686 produces one or more warning messages related to one or more potential consequences of each programming of the ICD energy level. For example, warning message producer 686 produces a warning message indicating the remaining amount of time, the remaining number of shock pulses deliverable, and/or the remaining number of programming performable before programming restriction module 676 disallows the programming of the ICD energy level. When programming restriction module 676 allows the programming of the ICD energy level according to the predetermined exception to the one or more predetermined restriction rules, warning message producer 686 produces a warning message indicating the inability to produce an estimated device longevity and/or the termination of the warranty on the device longevity provided by the manufacturer of the ICD.

In various specific embodiments, programming restriction module 676 includes any one or two of programming timer 678, shock pulse counter 680, and programming counter 682 to enforce the one or more predetermined restriction rules. In various specific embodiments, programming restriction module 676 includes one or more of programming timer 678, shock pulse counter 680, programming counter 682, exception code receiver 684, and warning message producer 686 to enforce the one or more predetermined restriction rules and allow the predetermined exception to the one or more predetermined restriction rules.

In one embodiment, the ICD stores its history of the ICD energy level programming. The history of the ICD energy level programming includes the time interval timed by programming timer 678, the number of defibrillation shock pulses delivered from the ICD counted by shock pulse counter 680, and/or the number of the programming of the ICD energy level counted by programming counter 682, depending on which one or more of the predetermined restriction rules are applied. After the initial activation of the ICD, at the beginning of each telemetry session during which external system 602 communicates with the ICD, external system 602 receives the history of the ICD energy level programming from the ICD. Before the end of the telemetry session, any change of the history of the ICD energy level programming is communicated to the ICD to update the history of the ICD energy level programming stored in the ICD. In another embodiment, external system 602 stores the history of the ICD energy level programming for the ICD. After the initial activation of the ICD, external system 602 recognizes that ICD, such as by a unique device identification code, and retrieves the history of the ICD energy level programming for that ICD from within external system 602. The history of the ICD energy level programming stored in external system 602 is updated in response to any change of that history.

User interface 642 is a specific embodiment of user interface 242 and includes a presentation device 646 and user input device 248. Presentation device 646 includes a display screen 674 to visually present the one or more estimated ICD performance parameters and the one or more warning messages. In one embodiment, display screen 674 is an interactive screen that also functions as part of user input device 248.

In one embodiment, user input device 248 allows the user to enter the ICD energy level parameter within a predetermined range. In another embodiment, user input device 248 allows the user to select the ICD energy level from a plurality of predetermined ICD energy levels within the predetermined range. In various embodiments, this predetermined range for the ICD energy level is approximately 5 joules to 100 joules. In various embodiments in which the shock pulses are delivered through intravenous/intracardiac electrodes, such as illustrated in FIG. 1, this predetermined range for the ICD energy level is approximately 5 joules to 50 joules. In a specific embodiment, user input device 248 allows the user to select the ICD energy level from approximately 31 joules and approximately 41 joules. In another specific embodiment, user input device 248 allows the user to select the ICD energy level from approximately 21 joules and approximately 31 joules. In another specific embodiment, user input device 248 allows the user to select the ICD energy level from approximately 21 joules, approximately 31 joules, and approximately 41 joules.

Figure 7:
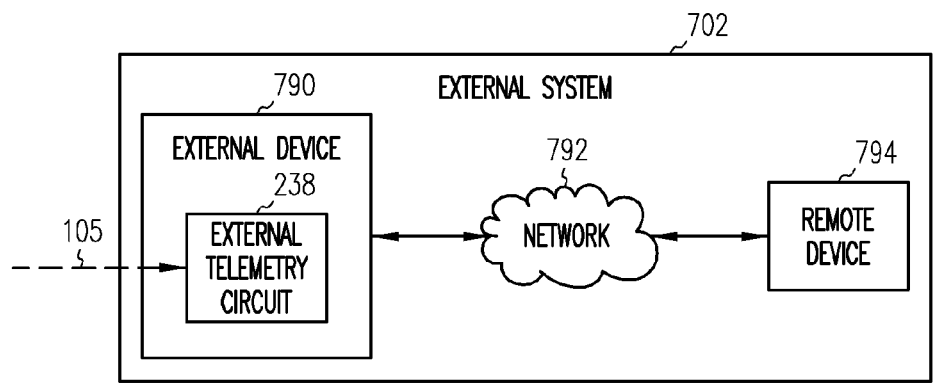
FIG. 7 is a block diagram illustrating a specific embodiment of the external system.

In one embodiment, external system 602 includes a programmer. In another embodiment, external system 602 includes a patient management system such as illustrated in FIG. 7. In various embodiments, either the programmer or the patient management system is used as external system 602 for programming the ICD energy level. For example, the user uses the programmer to program the ICD energy level during the implantation of the ICD, and then uses the patient management system to reprogramming the ICD energy level from a location remote from the patient.

External system 602 is a computer-based or microprocessor-based system. In one embodiment, ICD energy level programming module 244 or 644 is implemented by software. In another embodiment, ICD energy level programming module 244 or 644 is implemented by hardware, such as portions of an application specific integrated circuit or a programmable logic circuit. In another embodiment, ICD energy level programming module 244 or 644 is implemented by a combination of hardware and software.

FIG. 7 is a block diagram illustrating a specific embodiment of an external system 702, which is a specific embodiment of external system 602. As illustrated in FIG. 7, external system 702 is a patient management system including an external device 790, a telecommunication network 792, and a remote device 794. External device 790 is placed within the vicinity of the ICD and includes external telemetry system 238 to communicate with the ICD via telemetry link 105. Remote device 794 is in one or more remote locations and communicates with external device 790 through network 792, thus allowing a user to monitor and treat a patient from a distant location and/or allowing access to various treatment resources from the one or more remote locations. In one embodiment, after the implantation of the ICD, external system 702 allows a user to reprogram the ICD energy level from the distant location while the energy level programming is allowed by the one or more predetermined restriction rules.

Figure 8:
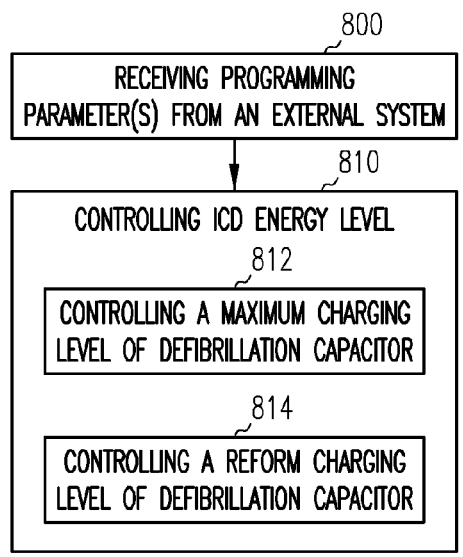
FIG. 8 is a flow chart illustrating an embodiment of a method for operating an ICD.

FIG. 8 is a flow chart illustrating an embodiment of a method for operating an ICD with energy level programmability. An example of such an ICD is ICD 110, including its various specific embodiments.

One or more programming parameters are received from an external system at 800. The external system allows a user to program the ICD. The ICD energy level is controlled according to the received one or more programming parameters at 810. The ICD energy level represents the maximum defibrillation energy deliverable by the ICD with each defibrillation shock pulse and is controlled by one or more ICD operational parameters. In one embodiment, an energy level parameter specifying the ICD energy is received from the external system at 800. The one or more ICD operational parameters are produced based on the energy level parameter. In a specific embodiment, a group of one or more ICD operational parameters is selected from a plurality of predetermined parameter groups each including one or more ICD operational parameters stored in the ICD. In another embodiment, the one or more ICD operational parameters are received from the external system at 800.

Examples of the ICD operational parameters include the maximum charging level and the reform charging level for the defibrillation capacitor(s) of the ICD. In one embodiment, as illustrated in FIG. 8, the ICD energy level is controlled by controlling the maximum charging level at 812 and controlling the reform charging level at 814. The maximum charging level and the reform charging level determines the device longevity of the capacitor charging time of the ICD.

Figure 9:
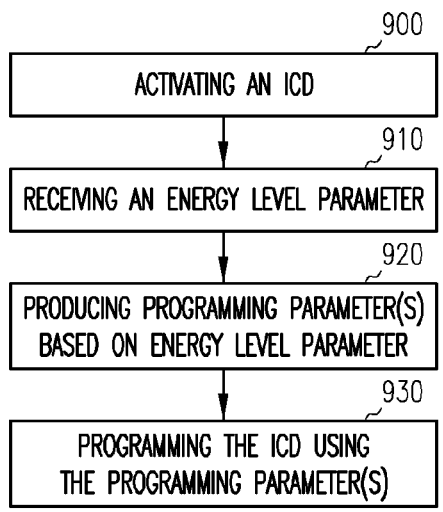
FIG. 9 is a flow chart illustrating an embodiment of a method for programming the ICD.

FIG. 9 is a flow chart illustrating an embodiment of a method for programming an ICD with energy level programmability. An example of such an ICD is ICD 110, including its various specific embodiments. The method is performed by an external system communicating with the ICD. An example of such an external system is external system 102, including its various specific embodiments.

The ICD is activated at 900. In various embodiments, an initial activation of the ICD is performed using the external system when the ICD is ready to be connected to a patient through one or more leads during the implantation. The ICD is ready for programming, including the programming of the ICD energy level, after the initial activation. An energy level parameter is received from a user at 910. The energy level parameter specifies the ICD energy level. One or more programming parameters controlling the ICD energy level are produced based on the energy level parameter at 920. In one embodiment, the one or more programming parameters include the energy level parameter. In another embodiment, the one or more programming parameters are produced based on the energy level parameter. The ICD is programmed using the one or more programming parameters at 930. After being programmed at 930, the ICD operates at the ICD energy level specified by the energy level parameter.

Figure 10:
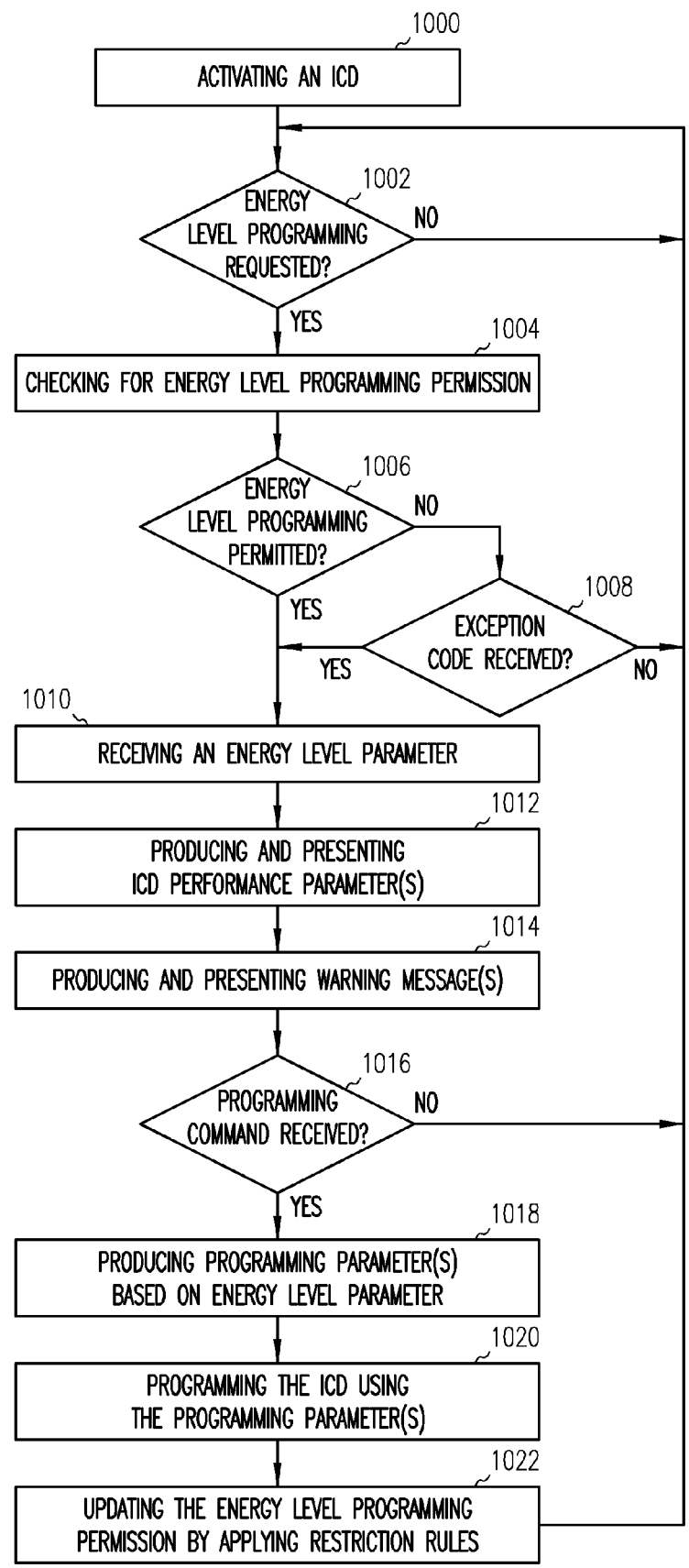
FIG. 10 is a flow chart illustrating a specific embodiment of the method for programming the ICD.

FIG. 10 is a flow chart illustrating a specific embodiment of the method for programming the ICD with energy level programmability. The method is a specific embodiment of the method illustrated in FIG. 9 and is performed by the external system communicating with the ICD.

The ICD is activated at 1000. After this initial activation, the user is allowed to program the ICD, including requesting a change in the ICD energy level. If the energy level programming is requested at 1002, whether such programming is permitted is checked at 1004. The permission is given according to one or more predetermined restriction rules. In various embodiments, the one or more restriction rules restrict the energy level programming to a limited period after the initial activation of the ICD. The limited period provide the user with the flexibility of reprogramming the ICD energy level when desired. In one embodiment, the limited period allows reprogramming of the ICD energy level in response to possible DFT changes while the lead(s) with defibrillation electrode(s) settle in the body and the electrode-tissue interface matures. On the other hand, this period is limited to ensure that the ICD has predictable device longevity, which is dependent on the programmed ICD energy level.

According to a first restriction rule, a time interval starting with the activation of the ICD is timed, and the energy level programming is permitted at 1006 if the time interval has not reached a predetermined programming time limit. In one embodiment, the predetermined programming time limit is in a range of approximately 1 week to 6 months, with approximately 3 months being a specific example. According to a second restriction rule, the number of defibrillation shock pulses delivered from the ICD since the activation of the ICD is counted, and the energy level programming is permitted at 1006 if the number has not reached a predetermined threshold number. In one embodiment, the number is in a range of approximately 3 to 15 defibrillation shock pulses, with approximately 10 defibrillation shock pulses being a specific example. According to a third restriction rule, the number of the programming of the ICD energy level performed since the initial activation of the ICD is counted, and the energy level programming is permitted at 1006 if the number has not reached a predetermined threshold number. In one embodiment, the number in a range of approximately 1 to 5 times of programming, with approximately 1 time of programming being a specific example. In various embodiments, any one or more of the first, second, and third restriction rules are applied at 1006. In various other embodiments, one or more restriction rules selected from the first, second, and third restriction rules as well as additional restriction rules are applied at 1006 to restrict the energy level programming to the limited period after the initial activation of the ICD.

If the energy level programming is not permitted at 1006 according to the one or more restriction rules, an exception rule to the one or more restriction rules is applied if one or more predetermined conditions are met. In one embodiment, as illustrated in FIG. 10, the exception rule includes the reception of an exception code. In a specific embodiment, the manufacturer of the ICD determines whether to provide the exception code upon a request made by the user. If provided, the user enters the exception code into the external system. If the exception code is not received by the external system at 1008, the energy level programming is terminated unless and until the user obtains the exception code and restarts the energy level programming from 1002.

If the energy level programming is permitted at 1006, or if the exception code is received at 1008, an energy level parameter is received from the user at 1010. The range of the value of the energy level parameter depends on the energy capacity of the ICD. In one embodiment, the value of the energy level parameter is in a range of approximately 5 joules to 100 joules. In one embodiment, the energy level parameter is selected from a plurality of predetermined energy levels at 1010. In one specific embodiment, the predetermined energy levels include approximately 21 joules and 31 joules. In another specific embodiment, the predetermined energy levels include approximately 31 joules and 41 joules. In another specific embodiment, the predetermined energy levels include approximately 21 joules, 31 joules, and 41 joules.

One or more ICD performance parameters are produced and presented at 1012 based on the energy level parameter received at 1010. In one embodiment, the ICD performance parameters include the device longevity and the capacitor charging time estimated based on the energy level parameter. In a specific embodiment, such ICD performance parameters are pre-estimated for a plurality of values of the energy level parameter and stored in the external system. After receiving the energy level parameter at 1010, the corresponding ICD performance parameters are produced by a mapping process using the value of the receive energy level parameter. In one embodiment, if the energy level parameter is received at 1010 following the reception of the exception code at 1008, no ICD performance parameter is produced because, for example, the device longevity is no longer reliably predictable.

One or more warning messages are produced at 1014. The one or more warning messages relate to potential consequences of each energy level programming, such as whether further energy level programming is permitted. If the energy level parameter is received at 1010 following the reception of the exception code at 1008, a warning message is produced to state the potential consequences of allowing the programming of the ICD energy level according to the exception rule. Examples of such consequences include the inability of producing the ICD performance parameters and/or the termination or modification of device warranty, if applicable.

After reviewing the ICD performance parameter(s) and the warning message(s), the user determine whether to program the ICD. If a programming command is received from the user at 1016, one or more programming parameters are produced based on the energy level parameter at 1018. In one embodiment, the one or more programming parameters include the energy level parameter. In another embodiment, the one or more programming parameters are produced based on the energy level parameter. The ICD is then programmed with the one or more programming parameters at 1020. The energy level programming permission is updated by applying the one or more restriction rules at 1022, following the programming of the ICD at 1020. Depending on the one or more restriction rules, the update may terminate or shorten the limited period during which the energy level programming is permitted. If the programming command is not received at 1016, the energy level programming is terminated without a change to the ICD energy level of the ICD.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable cardioverter defibrillator (ICD) configured to be communicatively coupled to an external system, the ICD comprising:

a defibrillation circuit configured to deliver defibrillation shock pulses each having an amount of energy programmed to a shock pulse energy level, the defibrillation circuit providing for a programmable ICD energy level and including a defibrillation capacitor, the ICD energy level being a maximum energy level up to which the shock pulse energy level is programmable, the defibrillation capacitor configured to store the energy for each of the defibrillation shock pulses;

an implant telemetry circuit configured to receive one or more programming parameters controlling the ICD energy level from the external system; and an implant controller coupled to the defibrillation circuit and the implant telemetry circuit, the implant controller including an energy level control module configured to control the ICD energy level by controlling a maximum charging level and a reform charging level using the one or more programming parameters, the maximum charging level being an energy level to which the defibrillation capacitor is charged in preparation for the delivery of each of the defibrillation shock pulses, the reform charge level is an energy level to which the defibrillation capacitor is charged in a reforming process when none of the defibrillation shock pulses is being delivered, wherein the ICD has an energy efficiency that is increased by decreasing a difference between the ICD energy level and the shock pulse energy level.

2. The ICD of claim 1, wherein the one or more programming parameters comprise an ICD energy level parameter specifying the ICD energy level, the implant controller comprises an operational parameter producer configured to produce one or more ICD operational parameters using the ICD energy level, and the energy level control module is configured to control the ICD energy level by controlling operation of the defibrillation circuit using the one or more ICD operational parameters.

3. The ICD of claim 2, wherein the defibrillation circuit further comprises
a capacitor charging circuit configured to charge the defibrillation capacitor to the maximum charging level in preparation for the delivery of the each of the defibrillation shock pulses, the maximum charging level being a parameter of the one or more ICD operational parameters,
and wherein the energy level control module comprises a maximum charging level controller to control the maximum charging level.

4. The ICD of claim 3, wherein the capacitor charging circuit is configured to charge the defibrillation capacitor to the reform charging level in the reforming process when none of the defibrillation shock pulses is being delivered, the reform charging level being a parameter of the one or more ICD operational parameters, and wherein the energy level control module comprises a reform charging level controller to control the reform charging level.

5. The ICD of claim 2, wherein the operational parameter producer is configured to select the one or more ICD operational parameters from a plurality of predetermined parameter groups based on the ICD energy level parameter.

6. The ICD of claim 1, wherein the one or more programming parameters comprise one or more ICD operational parameters, and the energy level control module is configured to control the ICD energy level by controlling operation of the defibrillation circuit using the one or more ICD operational parameters.

7. The ICD of claim 6, wherein the defibrillation circuit further comprises
a capacitor charging circuit configured to charge the defibrillation capacitor to the maximum charging level in preparation for the delivery of the each of the defibrillation shock pulses, the maximum charging level being a parameter of the one or more ICD operational parameters
and wherein the energy level control module comprises a maximum charging level controller to control the maximum charging level.

8. The ICD of claim 7, wherein the capacitor charging circuit is configured to charge the defibrillation capacitor to the reform charging level in the reforming process when none of the defibrillation shock pulses is being delivered, the reform charging level being a parameter of the one or more ICD operational parameters, and wherein the energy level control module comprises a reform charging level controller to control the reform charging level.

9. The ICD of claim 1, wherein the ICD energy level is programmable between approximately 5 joules and 50 joules.

10. The ICD of claim 9, wherein the ICD energy level is programmable between approximately 31 joules and 41 joules.

11. The ICD of claim 10, wherein the defibrillation capacitor has an energy density of approximately 6.50 joules per cubic centimeter.

12. The ICD of claim 1, further comprising a pacing circuit configured to deliver pacing pulses, and wherein the implant controller comprises a pacing controller configured to control the delivery of the pacing pulses by executing a pacing algorithm.

13. The ICD of claim 12, wherein the pacing controller is configured to control the delivery of the pacing pulses by executing a cardiac resynchronization therapy algorithm.

14. The ICD of claim 12, wherein the pacing controller is configured to control the delivery of the pacing pulses by executing a cardiac remodeling control therapy algorithm.

15. The ICD of claim 1, further comprising a sensing circuit configured to sense one or more cardiac signals, and wherein the implant controller comprises a defibrillation controller configured to control the delivery of the shock pulses by detecting and classifying tachyarrhythmia based on at least one signal of the one or more sensed cardiac signals.

16. The ICD of claim 1, further comprising a parameter storage circuit storing sets of values for ICD operational parameters, and wherein the implant controller comprises an operational parameter producer configured to select a set of values for the ICD operational parameters from the stored sets of values for the ICD operational parameters based on the received one or more programming parameters related to the ICD energy level, and the energy level control module is configured to control the ICD energy level by controlling operation of the defibrillation circuit using the one or more ICD operational parameters.

17. The ICD of claim 1, wherein the implant controller comprises a microprocessor or microcontroller circuit.

18. The ICD of claim 1, wherein the energy level control module comprises portions of a microprocessor or microcontroller circuit.

19. The ICD of claim 1, wherein the energy level control module comprises portions of an application specific integrated circuit.

20. The ICD of claim 1, wherein the energy level control module comprises portions of a programmable logic circuit.

* * * * *